(12) United States Patent
Ponciano et al.

(10) Patent No.: US 12,275,974 B2
(45) Date of Patent: Apr. 15, 2025

(54) SYNTHETIC ENZYME COMPLEXES FOR IN VITRO RUBBER PRODUCTION

(71) Applicant: The United States of America, as represented by the Secretary of Agriculture, Washington, DC (US)

(72) Inventors: Grisel P. Ponciano, Castro Valley, CA (US); Colleen M. McMahan, Sausalito, CA (US); Paul Hoeprich, Sacramento, CA (US); Patrick Scannon, San Francisco, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 214 days.

(21) Appl. No.: 17/469,744

(22) Filed: Sep. 8, 2021

(65) Prior Publication Data

US 2022/0073953 A1    Mar. 10, 2022

Related U.S. Application Data

(60) Provisional application No. 63/075,881, filed on Sep. 9, 2020.

(51) Int. Cl.
*C12N 9/00* (2006.01)
*C12N 9/10* (2006.01)
*C12P 5/02* (2006.01)

(52) U.S. Cl.
CPC ............ *C12P 5/026* (2013.01); *C12N 9/1085* (2013.01); *C12Y 205/0102* (2013.01)

(58) Field of Classification Search
CPC .. C12N 9/90; C12N 9/10; C12P 5/007; C12Y 205/0102; C12Y 205/0101; C12Y 503/03002
USPC ........................................................ 435/193
See application file for complete search history.

(56) References Cited

U.S. PATENT DOCUMENTS

| 9,303,272 B2 | 4/2016 | Adachi |
| 10,000,774 B2 | 6/2018 | Yamaguchi |
| 2017/0051313 A1 | 2/2017 | Inoue et al. |

OTHER PUBLICATIONS

Kisselev L., (Structure, 2002, vol. 10: 8-9).*
Kwiatkowski et al., (Biochemistry 38:11643-11650, 1999.*
Wristlock et al., (Quarterly Reviews of Biophysics 2003, vol. 36 (3): 307-340,).*
Davos et al., (Proteins: Structure, Function and Genetics, 2000, vol. 41: 98-107).*
NCBI, GenBank Accession No. XP _021653597.1, 'small rubber particle protein isoform XI [Hevea brasiliensis]', Jul. 19, 2017.
PCT International Search Report dated Dec. 24, 2021.

* cited by examiner

*Primary Examiner* — Robert B Mondesi
(74) *Attorney, Agent, or Firm* — John Fado; John Henri

(57) ABSTRACT

Disclosed herein are recombinant enzymes derived from various rubber-producing plants and the use of those enzymes in the production of natural rubber outside of plant tissues. Systems and methods for the utilization of these enzymes in the production of natural rubber are also provided.

25 Claims, 7 Drawing Sheets

Specification includes a Sequence Listing.

SYNTHETIC ENZYME COMPLEXES FOR IN VITRO RUBBER PRODUCTION

CROSS-REFERENCE

The present application claims priority to U.S. Provisional Patent Application Ser. No. 63/075,881 filed on Sep. 9, 2020 the content of which is expressly incorporated herein by reference.

BACKGROUND OF THE INVENTION

Field of Invention

Disclosed herein are recombinant enzymes derived from various rubber-producing plants and the use of those enzymes in the production of rubber polymer outside of plant tissues. Systems and methods for the utilization of these enzymes in the production of rubber polymer are also provided.

Background

Natural rubber (NR) is a U.S. Critical Agricultural Material (Public Law 95-592), sourced mainly from *Hevea brasiliensis* (rubber tree), at over 13 M tons global production in 2019 (Association of Natural Rubber Producing Countries), and is imported to meet essential industry, medicine, and defense needs. Despite the availability of petroleum-based synthetic rubber, NR has outstanding chemical and physical properties that render it irreplaceable in applications such as aircraft tires and medical devices (Mooibroek and Cornish 2000). Global industrial growth suggests the demand of this raw material will eventually outstrip production capabilities. Production has not changed appreciably in generations, i.e. established plantation farms, located largely in Southeast Asia, still plant and grow trees that are manually tapped to collect crude rubber latex material. Despite being an irreplaceable raw material, no real advances affecting NR supply have occurred. As such, we have developed novel systems and methodologies for the in vitro production of rubber polymer utilizing synthetic enzyme complexes (SECs) comprised of recombinant enzymes, optionally supported and stabilized by natural or synthetic lipids and other stabilizing agents, into mimetic rubber synthesis devices.

SUMMARY OF THE INVENTION

The present disclosure provides, in one embodiment, compositions for producing rubber polymer in vitro, comprising: 1) an isolated and purified cis-prenyltransferase; 2) an isolated and purified cis-prenyltransferase binding protein; 3) a reaction initiator; and 4) a substrate convertible into a polymer by said cis-prenyltransferase. In some embodiments, the compositions also comprise a lipid capable of forming a higher order structure, such as a micelle, a liposome, a mono-layer membrane, or a bilayer membrane. In specific embodiments, the lipid is DMPC. In additional embodiments, the compositions comprise an isolated and purified small rubber particle protein, such as one that is at least 99% identical to SEQ ID NO: 10 or SEQ ID NO: 12. In particular embodiments, the cis-prenyltransferase has a sequence at least 99% identical to SEQ ID NO: 2 or SEQ ID NO: 6. In some embodiments, the cis-prenyltransferase binding protein has a sequence at least 99% identical to SEQ ID NO: 4 or SEQ ID NO: 8. In some embodiments, the compositions also comprises a non-aqueous organic solvent. In still other embodiments, the compositions comprise a divalent cation, such as $Mg^{2+}$. In some embodiments, the initiator is an allylic pyrophosphate, such as FPP.

The present disclosure provides in another embodiment, methods of synthesizing rubber polymer, comprising the steps of: 1) providing reagents for synthesizing the rubber polymer; 2) providing the composition having a) an isolated and purified cis-prenyltransferase; b) an isolated and purified cis-prenyltransferase binding protein; c) a reaction initiator; and d) a substrate convertible into a polymer by said cis-prenyltransferase; and 3) contacting the reagents with the composition of claim 1 under conditions allowing for the production of the rubber polymer, thereby synthesizing the rubber polymer. In some embodiments of this method, the composition of step 2 further comprises a lipid capable of forming a higher order structure. In other embodiments of the methods, the composition of step 2 also contains an isolated and purified small rubber particle protein. In still other embodiments of the methods, the composition of step 2 also comprises an organic solvent.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The novel features of the invention are set forth with particularity in the claims. Features and advantages of the present invention are referred to in the following detailed description, and the accompanying drawings of which:

DETAILED DESCRIPTION OF THE INVENTION

Figure 1:
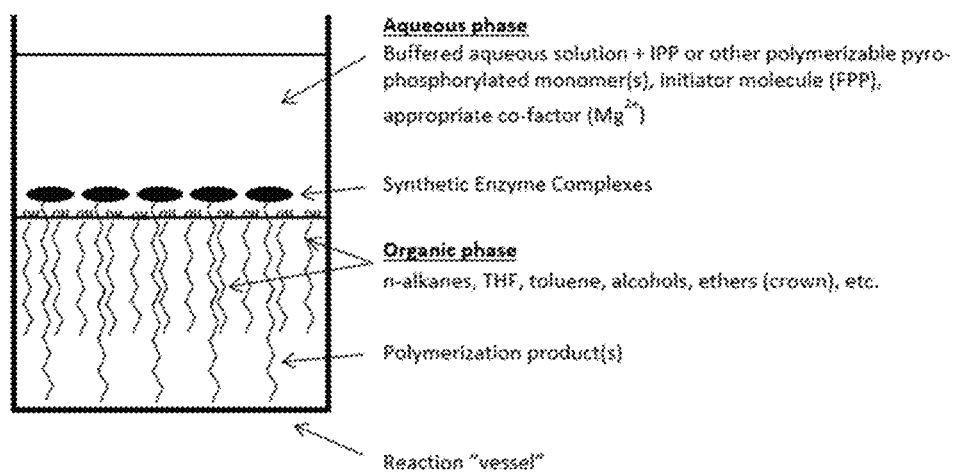
FIG. 1 provides a pictorial representation of one potential embodiment of a system for producing rubber polymer ex vivo.

Disclosed herein are rubber-polymer-producing synthetic molecular complexes. These synthetic complexes may be comprised of several forms, e.g., 1) lipid/protein monolayer spherical particles (as found in nature), 2) lipid/protein bilayer sheets, 3) lipid/protein single layer sheets/films, 4) micelles, 5) liposomes, 6) nanolipoprotein particles (NLP), vesicles used to stabilize membrane-bound enzymes, and 7) molecular complexes bound to solid surfaces including beads as support structures. Particular embodiments of the present subject invention utilize a minimally required enzyme component, namely: 1) a cis-prenyl transferase (CPT), and 2) a cis-prenyl transferase binding (CBP) protein. Proteins utilized are typically produced by purification from recombinant microbes. In preferred embodiments, the two enzymes are incorporated into a membrane composed of lipids. Rubber-polymer-producing systems disclosed herein can also contain additional components for stabilization of the system, such as a Small Rubber Particle Protein (SRPP), a Rubber Elongation Factor (REF), or synthetic apolipoproteins (e.g., recombinant Apo-A1, human cat #SRP6410, Sigma-Aldrich). Other known rubber particle proteins such as allene oxide synthase (AOS), can also be utilized in the rubber-polymer-producing systems and methods disclosed herein. The systems, methods, and compositions provided herein lack certain components of plant-derived natural rubber particles, including, but not limited to, ATP synthase subunits and transporter-like proteins.

Rubber polymers of the present disclosure are like natural rubber, for example have high molecular weight and high stereospecificity, but the ex vivo material is likely to be substantially purer than plant derived natural rubber. Additionally, molecular weight distribution might be different between ex vivo rubber polymers and NR. Ex vivo rubber polymer can also be made utilizing different initiator molecules, thus potentially having an overall different polymer structure at the end group. Such initiators can potentially contain reactive moieties. Systems described herein can also be fed alternative monomers, which are also polymerizable by the synthetic complex to create new synthetic polymers with high stereospecificity; can be fed a mixture of monomers to create random and block copolymers or branched polymers; and can be fed at the end of a reaction to "cap" the polymer, resulting in a chain-end functionalized polymer. The rubber-polymer-producing systems (i.e., an engineered rubber particle) can be used to produce ex vivo (plant-free) rubber polymer from bio-derived monomers (e.g. IPP, bio-isoprene), for example using cellulosic sugar and the like as a starting material. The subject synthetic technology can be used to complement current rubber production, particularly for specialized applications such as medical supplies, due to the likelihood of obtaining a pure product lacking in allergenic proteins, or micro/nano systems inaccessible with current technology. Further, it provides an additional layer of supply security and enables rubber polymer production in extreme environments such as deep ocean and outer space.

Constructs containing the engineered rubber particles described herein can be housed in a complex that enables application of industrial biotechnology production/manufacturing tenets to ex vivo production, allowing for the development of scalable processes leading to lower overall raw material and production costs.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N. Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991. Standard reference literature teaching general methodologies and principles of fungal genetics useful for selected aspects of the invention include: Sherman et al. "Laboratory Course Manual Methods in Yeast Genetics", Cold Spring Harbor Laboratory, Cold Spring Harbor, N.Y., 1986 and Guthrie et al., "Guide to Yeast Genetics and Molecular Biology", Academic, New York, 1991.

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted.

As used in the specification and claims, use of the singular "a", "an", and "the" include plural references unless the context clearly dictates otherwise.

The terms isolated, purified, or biologically pure as used herein, refer to material that is substantially or essentially free from components that normally accompany the referenced material in its native state. One non-limiting example of an isolated substance is a recombinant protein purified from a suitable host microbe producing the protein.

The term "about" is defined as plus or minus ten percent of a recited value. For example, about 1.0 g means 0.9 g to 1.1 g and all values within that range, whether specifically stated or not.

The amounts, percentages and ranges disclosed herein are not meant to be limiting, and increments between the recited amounts, percentages and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein).

The terms "polypeptide, peptide or protein" refer to polymers in which the monomers are amino acid residues which are linked through amide bonds. When the amino acids are alpha-amino acids, either the L-optical isomer or the D-optical isomer can be used. The terms are used interchangeably herein. These terms apply to amino acid polymers in which one or more amino acid residues are an artificial chemical mimetic of a corresponding naturally occurring amino acid, as well as to naturally occurring amino acid polymers and non-naturally occurring amino acid polymers.

The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant cells may express genes/polynucleotides that are not found within the native (non-recombinant or wild-type) form of the cell or express native genes in an otherwise abnormal amount-over-expressed, under-expressed or not expressed at all-compared to the non-recombinant or wild-type cell or organism.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch, J Mol Biol, (1970) 48:3, 443-53). A computer-assisted sequence alignment can be conveniently performed using a standard software program such as GAP which is part of the Wisconsin Package Version 10.1 (Genetics Computer Group, Madison, Wisconsin, USA) using the default scoring matrix with a gap creation penalty of 50 and a gap extension penalty of 3.

The phrase "high percent identical" or "high percent identity", and grammatical variations thereof in the context of two polynucleotides or polypeptides, refers to two or more sequences or sub-sequences that have at least about 80%, identity, at least about 81%, 82%, 83%, 84%, 85%, 86%, 87%, 88%, 89%, 90%, 91%, 92%, 93%, 94%, 95%, 96%, 97%, 98%, 99%, or 100% nucleotide or amino acid identity, when compared and aligned for maximum correspondence, as measured using a sequence comparison algorithm or by visual inspection. In an exemplary embodiment, a high percent identity exists over a region of the sequences that is at least about 16 nucleotides or amino acids in length. In another exemplary embodiment, a high percent identity exists over a region of the sequences that is at least about 50 nucleotides or amino acids in length. In still another exemplary embodiment, a high percent identity exists over a region of the sequences that is at least about 100 nucleotides or amino acids or more in length. In one exemplary embodiment, the sequences are high percent identical over the entire length of the polynucleotide or polypeptide sequences.

Proteins

Proteins utilized in the methods, systems and processes provided herein typically derive from natural sources, but also include modified versions of such proteins. Proteins can be enzymes, such as a cis-prenyltransferase or a cis-prenyltransferase binding protein from any source, including an NR-producing plant. Proteins can also be a trans-prenyl transferase or trans-prenyl transferase binding protein from any source, including a trans-NR (*Gutta percha*) producing plant. Proteins can also be non-enzymatic proteins such as Small Rubber Particle Protein (SRPP), which is thought to provide structural support to enzymes involved in NR production. Typically, because of the quantities of proteins desired for large-scale in vitro production of NR, proteins are produced recombinantly, and not isolated from naturally occurring sources. However utilized, proteins of the present invention are not incorporated into a plant rubber particle, where rubber synthesis is known to occur in plants and in enzymatically active rubber particles extracted from plants.

Any bacterial or eukaryotic recombinant protein production system can be utilized in practicing the instant disclosure, including, but not limited to *E. coli*, yeasts, filamentous fungi, insect cells, and mammalian cells. In the construction of a recombinant protein production system, it may be necessary or desirable to modify a source DNA coding region to a codon-optimized version in order to achieve desired expression and production levels. Such modifications are well within the capabilities of one skilled in the art. If desired, cell-free systems can also be utilized for protein production.

Table 1 provides a brief list of exemplary proteins that can be utilized in practicing the methods, systems and compositions provided herein. The listed proteins are derived from two NR-producing plants (guayule and *Hevea* rubber tree), however, orthologs from other species are known and can be utilized, including from other known NR-producing plants (e.g., Russian dandelion (*Taraxacum kok-saghyz*), lettuce (*Lactuca sativa*), rubber fig tree (*Ficus elastica*), *Eucommia ulmoides*, and *Castilla elastica*, other plants, and non-plant species (e.g., *Lactarius volemus, Lactarius chrysorrheus*, and *Lactarius hygrophoroides*). In the case of transferase proteins based on *Palaquia gutta*, a trans-polyisoprene polymer would be produced.

TABLE 1

Exemplary Recombinant Proteins

| Enzyme Name | Original Source | SEQ ID NO: |
|---|---|---|
| cis-prenyltransferase (CPT) | *Partheniuum argentatum* (guayule) | SEQ ID NO: 2 |
| cis-prenyltransferase binding protein (CBP) | *P. argentatum* | SEQ ID NO: 4 |
| cis-prenyltransferase (HRT2) | *Hevea brasiliensis* (rubber tree) | SEQ ID NO: 6 |
| cis-prenyltransferase binding protein (HRBP) | *H. brasiliensis* | SEQ ID NO: 8 |
| Small rubber particle protein (PaSRPP) | *P. argentatum* | SEQ ID NO: 10 |
| Small rubber particle protein (HbSRPP) | *H. brasiliensis* | SEQ ID NO: 12 |
| Rubber Elongation Factor (REF) | *H. brasiliensis* | SEQ ID NO: 14 |

Reaction Parameters

Reactions described herein can be modified by the skilled artisan to achieve efficiency or other desired outcomes. Such modifications are known in the art. Exemplary modifications include reaction pH between 6.5 and 9.5, including any and all specific pH values between these endpoints, such as 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, and 9.5. Additionally, reaction temperature is an exemplary modification, such as temperatures at 10° C.-35° C., including any and all specific values between these two endpoints, such as 10° C., 10.5° C., 11° C., 11.5° C., 12° C., 12.5° C., 13° C., 13.5° C., 14° C., 14.5° C., 15° C., 15.5° C., 16° C., 16.5° C., 17° C., 17.5° C., 18° C., 18.5° C., 19° C., 19.5° C., 20° C., 20.5° C., 21° C., 21.5° C., 22° C., 22.5° C., 23° C., 23.5° C., 24° C., 24.5° C., 25° C., 25.5° C., 26° C., 26.5° C., 27° C., 27.5° C., 28° C., 28.5° C., 29° C., 29.5° C., 30° C., 30.5° C., 31° C., 31.5° C., 32° C., 32.5° C., 33° C., 33.5° C., 34° C., 34.5° C., 35° C. Another exemplary modification is alteration of the buffer system, such as Tris-HCl buffers at concentrations between 10-150 mM, including any and all specific concentrations between these two endpoints, such as 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 105 mM, 110 mM, 115 mM, 120 mM, 125 mM, 130 mM, 135 mM, 140 mM, 145 mM, and 150 mM. Additional exemplary modifications include the presence or absence of reaction enhancers and surface area, such as cobalt resin present in the reaction and/or the presence of beads or matrices.

Proteins of the present invention can be combined with multiple additional components as desired for fine-tuning of ex vivo rubber-polymer-producing reactions. One non-limiting, exemplary embodiment is represented in FIG. 1, which shows various optional components of systems utilizing disclosed proteins, enzymes and combinations thereof. Polymerization rates and efficiencies are expected to be impacted, and therefore potentially optimized, by judicious selection of 1) pH (pH 6.5-9.5), 2) magnesium or other divalent cation cofactor choice and concentration (1-20 mM), 3) lipid choice (saturated, unsaturated, furan structures), 4) lipid concentration (0.5-5%), 5) temperature (10° C. to 35° C.), and 6) presence or absence of one or more solvents.

Lipids

Lipids useful in practicing the instant invention can be natural or synthetic, typically possessing both hydrophilic and hydrophobic properties that in an aqueous environment assemble in a lipid monolayer or bilayer structure. Such polar lipids have a hydrophilic moiety and a hydrophobic moiety, as exemplified by phospholipids (e.g., PE, PC, PI, PS, PA, DMPC, DOPE, DOPC, DPPC), glycolipids (e.g., glycosphingolipids), sterols (e.g., sitosterol), sphingolipids (e.g., ceramides), neutral lipids (e.g., triglycerides, ether lipids, furanoid lipids, lipids with hydroxy fatty acids), and alkylphosphocholines. Specific lipids that can be utilized include, but are not limited to Phosphatidylethanolamine (PE), phosphatidylcholine (PC), phosphatidylinositol (PI), phosphatidylserine (PS), phosphatidic acid (PA), dimyristoylphosphatidylcholine (DMPC), dioleoylphosphoethanolamine (DOPE), dioleoylphosphatidylcholine (DOPC), and dipalmitoylphosphatidylcholine (DPPC). Additional lipids are widely known in the art and can be selected by the skilled artisan as suitable for particular embodiments (e.g., high temperature reactions, low temperature reactions, high pH reactions, etc.).

Reaction initiators that can be utilized in practicing the instant disclosure include any now known, or discovered in the future. Non-limiting exemplars of initiators include allylic pyrophosphates such as FPP, di-methyl allyl PP (DMAPP), geranyl PP (GPP), geranyl geranyl PP (GGPP), HPP, derivatives of allylic pyrophosphates (e.g., benzophenone), and FOO. For embodiments utilizing an organic compound for a bi-phasic system, an appropriate organic compound (e.g., organic solvent) can be chosen by the skilled artisan. Exemplary compounds include benzene, n-hexane, cyclohexane, tetrahydrofuran, chloroform, and octanol.

Alternative Monomers/Initiators

The native rubber transferase complex is known to accept a wide range of initiators; when such initiators are introduced to purified washed rubber particles IPP is polymerized. Alternative initiators include dimethyl allyl pyrophosphate (DMAPP), geranyl pyrophosphate (GPP), geranyl geranyl pyrophosphate (GGPP), hexa-hepta prenyl pyrophosphate (H-HPP) and others (Mau and Cornish U.S. Pat. No. 8,013,213; Mau et al. 2003). Even initiator analogs such as benzophenone derivatives of DMAPP and GPP successfully initiate polymerization despite the presence of the sizable R group (Xie et al. 2008). A similar range of alternative initiators may be used with the subject synthetic complexes, resulting in polymers with a functionalized (alpha) end group. In an analogous manner, a variety of pryophosphorylated molecules can serve as alternative monomers in the subject synthetic complexes to synthesize a variety of previously undescribed polymeric materials. For example, polymerization of (E-1)-hydroxy-2-methyl-2-butenyl-4-pyrophosphate (HMBPP) by the synthetic complex results in a hydroxy functionalized polyisoprene. Based on the structure of IPP, the native monomer, one group of alternative monomers that can be utilized in practicing the instant invention are derivatives of IPP with substitution at the R5, methyl group position, per Formula I. Non-limiting examples of such IPP derivatives include hydroxy IPP (R5=hydroxy group), aniline IPP (R5=aniline), and styrene IPP (R5=styrene).

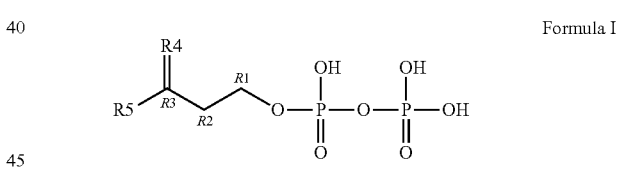

Formula I

Having generally described this invention, the same will be better understood by reference to certain specific examples, which are included herein to further illustrate the invention and are not intended to limit the scope of the invention as defined by the claims.

EXAMPLES

Example 1

Production and Isolation of Recombinant Proteins

Proteins CPT (SEQ ID NO: 2), CBP (SEQ ID NO: 4), and PaSRPP (SEQ ID NO: 10) were produced in *E. coli*, extracted by chemical lysis, and purified by affinity chromatography. Every step of the process was monitored by denaturing polyacrylamide gel electrophoresis (PAGE) and western blot analysis.

These proteins derived from guayule (Table 1) were cloned into pET29a (+) (NOVAGEN) protein expression vector and transformed into T7 Express (New England Biolabs, Ipswich, MA) *E. coli* cells. Bacterial cultures were grown at 37° C. in 50 mL Luria Bertani broth supplemented with 30 µg/mL of Kanamycin under moderate shaking until reaching a growth of optical density between 0.3-0.4 at $A_{600}$. Protein synthesis was elicited with a final concentration of 0.4 mM IPTG for 30 min. Bacterial proteins were extracted with B-PER bacterial protein extraction reagent supplemented with DNaseI, lysozyme, and proteinase cocktail (Pierce Biotechnology, Rockford IL). Recombinant proteins were affinity purified by bulk with S-protein agarose following manufacturer recommendations (Sigma-Millipore, USA), concentrated with Amicon 10K filters (Amicon, USA), and buffer exchanged with ZEBAspin columns (Pierce Biotechnology, Rockford IL) to replace the buffer with IPP incorporation assay buffer. Total protein concentration was estimated with QUICK START Bradford Protein Assay (Bio-Rad, Hercules, CA).

After normalizing protein concentrations, proteins were run on a 4-12% NUPAGE Bis-Tris pre-cast polyacrylamide gel under reducing conditions (Life Technologies, Carlsbad, CA) and detected with Bio-Safe Coomassie stain (Bio-Rad, Hercules, CA). For western blot, proteins from the PAGE gel were transferred to a PVDF membrane, blocked for 1 hr at room temperature or overnight at 4° C. with SUPERBLOCK (Pierce Biotechnology, Rockford IL) blocking buffer, incubated for 1 hr with 10 ng/ml anti S-Tag monoclonal antibodies (EMD Millipore, Temecula, CA), following 30 min incubation with 2 ng/ml anti Mouse IgG-HRP conjugate (Bio-Rad, Hercules, CA), and final chemiluminescent detection with SUPERSIGNAL Femto Maximum Sensitivity Substrate (Thermo Scientific, Waltham, MA). Membrane was wrapped with plastic wrap and exposed to CL-XPOSURE film (Thermo Scientific, Waltham, MA) for 10-30 s. Protein molecular weight markers are PAGERULER prestained protein ladder (Invitrogen, USA).

HRT2 (SEQ ID NO: 6), HRBP (SEQ ID NO: 8), and HbSRPP (SEQ ID NO: 12) proteins derived from the rubber tree (Table 1) were cloned into pET (NOVAGEN) protein expression vector pET32b (+) and transformed into E. coli cells (BL21 (DE3) (New England Biolabs, Ipswich, MA). Bacterial cultures were grown at 37° C. in 50 mL Luria Bertani broth supplemented with 50 µg/mL carbenicillin under moderate shaking until reaching a growth of appropriate optical density at $A_{600}$ (0.6). Protein synthesis was elicited with a final concentration of 0.4 mM IPTG for 2-6 h. Bacterial proteins were extracted by chemical lysis using CELLYTIC (Sigma-Millipore, USA). Recombinant proteins were affinity purified (by column fractionation with Cobalt Resin (Thermo Fisher, USA). When needed, purified proteins were concentrated with Amicon 10K filters (Amicon, USA) or buffer exchanged with ZEBA spin columns (Pierce Biotechnology, Rockford IL) to replace the buffer with IPP incorporation assay buffer.

Every step of the protein extraction and purification process was monitored by standard denaturing polyacrylamide gel electrophoresis (PAGE) and western blot analysis. For western blot, proteins from the PAGE gel were transferred to a PVDF membrane, blocked for 1 hr at room temperature or overnight at 4° C. with SUPERBLOCK (Pierce Biotechnology, Rockford IL) blocking buffer. The membrane was incubated with anti HIS-tag primary antibody overnight at 4° C., then with horse radish peroxidase-secondary antibody at room temperature for 1 h prior to colorimetric development with CN/DAB substrate kit (Thermo Fisher, USA).

Example 2

Assembly of Enzyme Complex and Polymerization

Recombinant proteins CPT (SEQ ID NO: 2) and CBP (SEQ ID NO: 4) (250 ng-14 µg) were incubated with an equal volume of 12 mM DMPC (1,2-Dimyristoyl-sn-glycero-3-phosphocholine) and 20 mM cholate for 1 hr at room temperature. A 20 µL aliquot of the self-assembled protein/lipid complex was transferred to a centrifugal filter unit (MilliporeSigma Model Ultrafree® MC-VV) containing 20 µM farnesyl pyrophosphate (FPP) initiator, 1 mM unlabeled IPP and 0.9 nmol (55 mCi mmol-1) $^{14C}$-IPP in buffer (100 mM Tris-HCl, pH 7.5; 1.25 mM $MgSO_4$, 5 mM dithiothreitol) in a total reaction volume of 50 µL. Under these conditions, the initiator molecule farnesyl pyrophosphate (FPP) binds to the rubber transferase enzyme complex, and the polymerization, proceeds by successive condensation reactions of the monomer-isopentenyl pyrophosphate (IPP, both 14C-labelled and un-labelled).

The reactions, performed in triplicate, were incubated at room temperature for 3-4 h, stopped with addition of 40 mM ethylene diaminetetraacetic acid (EDTA), pH 8.0, and washed by centrifugation at 14,000 rpm three times with water for removal of unincorporated monomer (IPP). For the biphasic condition, the same reaction was conducted and 25 µL of either butanol or hexane was carefully layered on top of the reaction. For product molecular weight analysis, the same reaction was conducted without radioactive $^{14C}$-IPP monomer.

Figure 2:
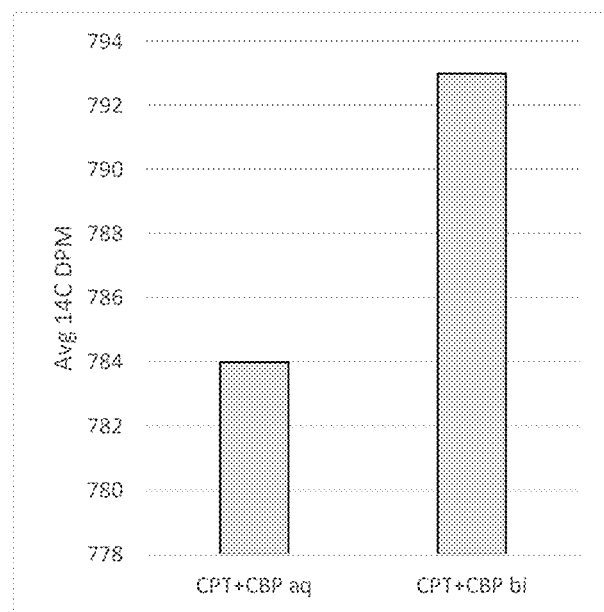
FIG. 2 provides graphic representation of the results of an $^{14}C$-IPP incorporation assay of recombinant CPT and CBP under two different environmental conditions, aqueous (aq) and aqueous-organic biphasic (bi).

Following the IPP/14C IPP polymerization, the filter unit containing the washed product was inserted in a vial containing 2 mL BD Cocktail (Fisher Sci., Model ScintiVerse, Santa Clara, CA) and the amount of [14C]-IPP in each individual filter was quantified by scintillation counting (Beckman Coulter, Model LS 6500, Brea, CA). The average value of the 14C disintegrations per minute (DPM) count quantifies the cis-prenyl transferase activity of the reaction mixture, as has been well established in native systems (Xie et al, Phytochem. (2008) 69:2539-45; Brasher et al., The Plant J. (2015) 82:903-14; Qu et al, J. Biol. Chem., (2015) 290:1898-1914; Placido et al, Front. Plant Sci. (2019) doi.org/10.3389/fpls.2019.00760). Results are shown in FIG. 2 for experiments utilizing CPT (SEQ ID NO: 2) and CBP (SEQ ID NO: 4) derived from guayule.

As stated above, the average value of the 14C disintegrations per minute (DPM) count from the polymers produced quantifies the cis-prenyl transferase enzymatic activity. The DPM values for a series of experiments wherein initiator and monomer molecules were introduced into reaction vessels containing various enzymatic and stabilizing components are shown below. The higher the value, the more IPP incorporated into the product under the specific conditions and times. CPT (SEQ ID NO: 2) enzyme and CBP (SEQ ID NO: 4) were expressed in E. coli and affinity purified. Activity of the proteins were tested by mixing them in equal amounts on a microfuge tube in the presence of the synthetic phospholipid 1,2-Dimyristoyl-sn-glycero-3-phosphocholine (DMPC) to stabilize these two membrane-associated proteins.

The $^{14C}$-IPP incorporation assay is an in vitro enzymatic assay to test the activity of CPTs. In this assay, the molecule farnesyl pyrophosphate (FPP) binds to the CPT enzyme to initiate the reaction, followed by successive condensation reactions of isopentenyl pyrophosphate (IPP, both $^{14C}$-labelled and un-labelled) that synthesizes an isoprene polymer of varying length. After 3-4 hrs of incubation at room temperature with gentle shaking, the reaction is stopped, and unpolymerized FPP and IPP monomers removed from the reaction product. To evaluate $^{14C}$-IPP incorporation into the final isoprene polymer, the reaction is mixed with scintillation fluid and the radiation emitted by the incorporated $^{14C}$-IPP is detected on a scintillation counter in the form of DPM (disintegrations per minute) units.

We conducted the $^{14C}$-IPP incorporation assay under two different environmental conditions: aqueous (aq) and aqueous-organic bi-phasic (bi). The reason for testing these two conditions is the isoprene polymer is hydrophobic in nature and the aqueous environment is predicted to be a suboptimal one for effective in vitro synthesis. The addition of an organic solvent layer (such as n-hexane or butanol) on top of the aqueous reaction can provide an environment where the polymer can easily be solubilized without hindering the reaction.

Similar experiments were run utilizing HRT2 (SEQ ID NO: 6) and HRBP (SEQ ID NO: 8) either alone or in combination with SRPP (SEQ ID NO: 10) and an NLP (made from 5 mg DMPC and 1 mg SRPP). Pre-incubation was performed for 1 hour at room temperature. Results are shown in Table 2 for experiments utilizing HRT2 (SEQ ID NO: 6) and HRBP (SEQ ID NO: 8).

TABLE 2

IPP incorporation results utilizing rubber tree derived proteins

| Reaction components and conditions | Average DPM |
|---|---|
| HRT2 + HRBP, biphasic | 346 |
| HRT2 + HRBP + DMPC, biphasic | 4024 |
| HRT2 + HRBP + SRPP-NLP (no pre-incubation), aqueous | 55 |
| HRT2 + HRBP + SRPP-NLP (pre-incubation), biphasic | 258 |

Example 3

Characterization of Reaction Products

Gel permeation chromatography (GPC) i.e. liquid chromatography with continuous tetrahydrofuran (THF) solvent phase, using size exclusion separation columns and multiple detectors, was used to determine the quantity and molecular weight of the products of various in vitro reactions. Reaction Products from Synthetic Complex HRT2+HRBP, Biphasic Reaction Triplicate unfiltered reaction mixtures were combined for a total 150 µL volume, to which 300 µL THF was added. The mixture was gently shaken, for 12-18 hours solubilization time, then a 100 µL aliquot was withdrawn from the (upper) organic phase, placed into an autosampler vial insert, and 50 µL load injected onto the columns and size exclusion separated (THF continuous phase, 1.0 mL/min) by two Agilent PL gel 10 µm Mixed-B columns in series at 35° C. Peak elution detected by refractive index (RID; Agilent 1260 Infinity, dn/dc=0.129) and light scattering (LS) (DAWN Heleos-II, Wyatt Technology Corp., Santa Barbara, CA) detectors and represents the polyisoprene. The molecular weights were calculated from the RID and LS peaks by Astra 6.1 (Wyatt Technology).
Product Mass and Molecular Weight Plant dolichols and polyprenols have variable molecular weights. Jankowski et al, (Plant Physiol. (1994) 143:448-452) report up to 25 isoprene units, or 125 carbon atoms, from various plant sources. Brasher et al. (supra) report up to 19 units, or about 90 carbon atoms. These correspond to molecular weight size in the 1500-2000 Da range. We have produced much longer chain polyisoprenes utilizing recombinant enzymes.

Figure 3:
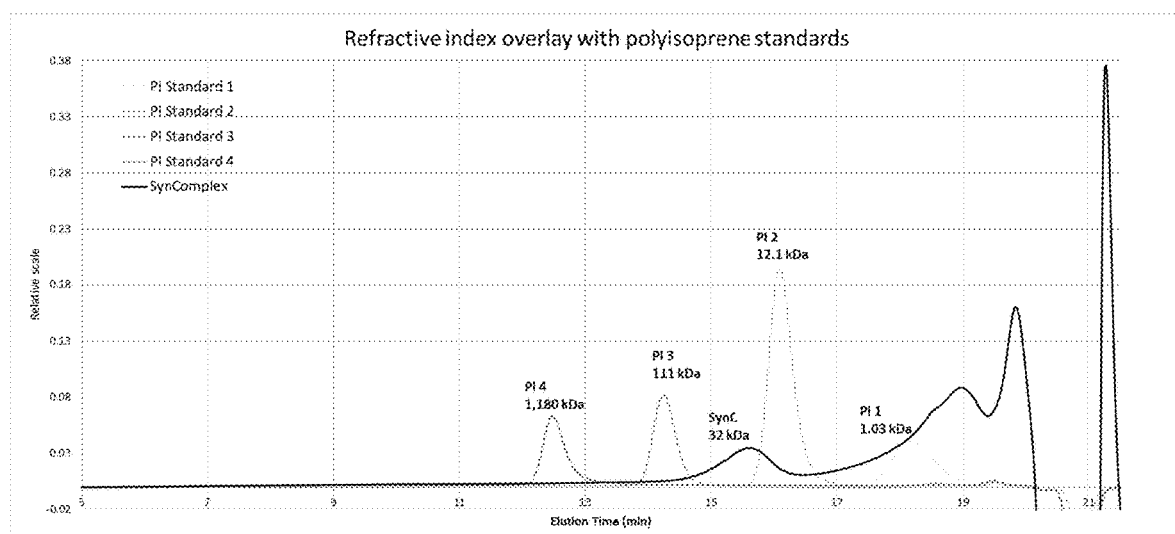
FIG. 3 provides a gel permeation chromatogram tracing from a refractive index detector showing reaction products of an in vitro rubber polymer synthesis reaction.

In the example HRT2+HRBP, biphasic experiment, recombinant proteins HRT (SEQ ID NO: 6) and HRBP (SEQ ID NO: 8) were prepared and combined with DMPC lipid to form complexes that polymerized and added cold IPP monomer with hexane as the organic phase. The molecular weight of the product was determined. Results confirm the presence of polyisoprene of ~32,000 Da (Mp), ranging from below 10,000 to 100,000 Da (SynC peak below). Integration of the peak at yielded 6.77 µg of product in this molecular weight range. Lower molecular weight product was also produced, as evident by peaks at and above 19 minutes elution time. Negative peaks between 20-24 minutes are an artifact of sample injection. Chromatograms shown in FIG. 3 are from the Refractive index detector, set to dn/dc of 0.129, which corresponds to the known polyisoprene value (Jackson et al, J Appl. Polymer Sci. (1996), 61:865-874).

Figure 4:
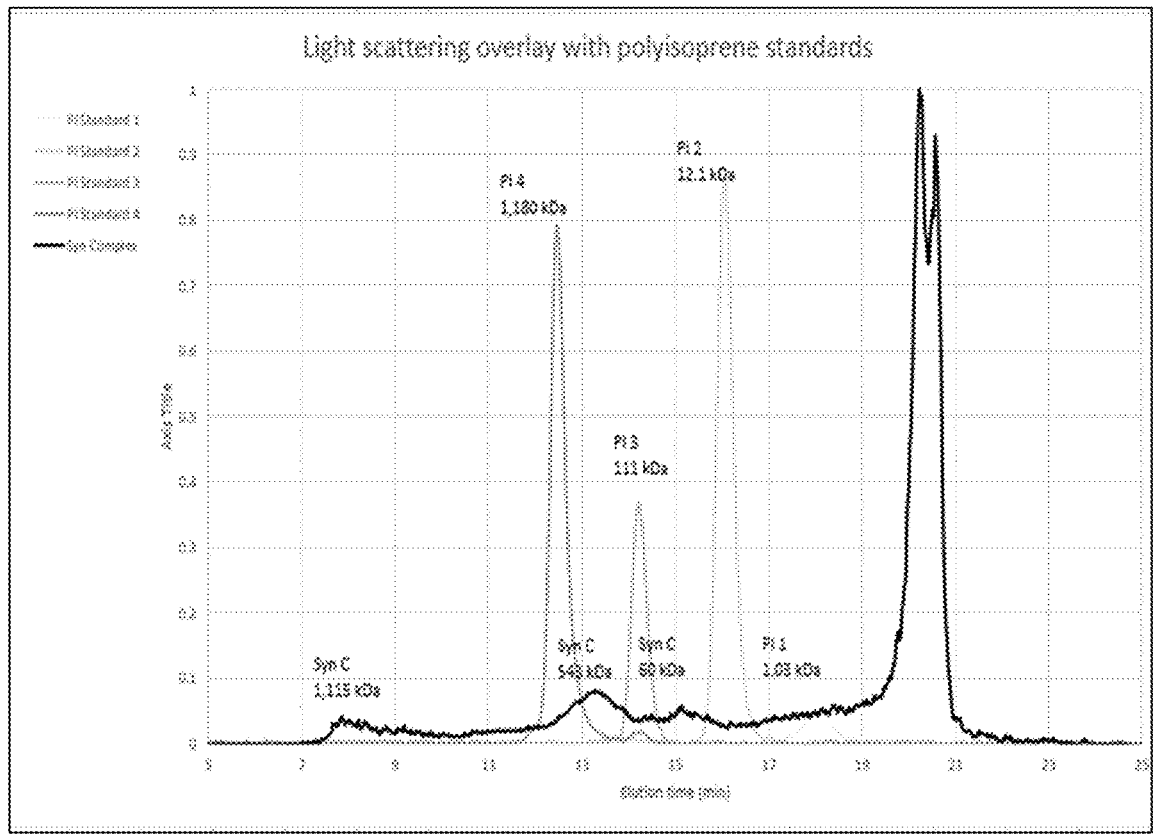
FIG. 4 provides a gel permeation chromatogram tracing from a light scattering detector showing reaction products of an in vitro rubber polymer synthesis reaction.

Results also suggest the presence of a very small amount of a very high molecular weight product, Mp of about 1,115,000 Da (Mp). Chromatograms shown in FIG. 4 are from the light scattering detector. Due to the very low amount of material, the quantity could not be determined. It is known in the art that light scattering detectors are more sensitive in the high molecular weight range, while refractive index detectors are more sensitive in the lower molecular weight range (Jeng et al, Appl. Polymer Sci. (1993) 49:1359-1374).

Example 4

Assembly of Enzyme Complex and Polymerization II

HRT2 (SEQ ID NO: 6) and HRBP (SEQ ID NO: 8) were expressed in E. coli and affinity purified. Activity of the proteins were tested by mixing them in equal amounts on a microfuge tube in the presence of the soy phosphatidylcholine (PC) to stabilize these two membrane-associated proteins. Recombinant proteins (15 µg) were mixed with 1% (w/v) soy phosphatidylcholine (PC) and protein/lipid complex was transferred to a centrifugal filter unit (MilliporeSigma Model Ultrafree® MC-VV) containing 5 µM farnesyl pyrophosphate (FPP) initiator, 1 mM unlabeled IPP and 0.9 nmol (55 mCi mmol-1) $^{14C}$-IPP in buffer (100 mM Tris-HCl, pH 8; 1.25 mM MgSO$_4$, 20 mM 2-mercaptoethanol) in a total reaction volume of 100 µL. Negative control reactions included the same components plus EDTA to 40 mM final concentration.

The reactions, performed in triplicate, were incubated at room temperature for ~18 h, stopped with addition of 40 mM ethylene diaminetetraacetic acid (EDTA), pH 8.0, and washed by centrifugation at 14,000 rpm four times with water for removal of unincorporated monomer (IPP). Following the IPP/$^{14C}$-IPP polymerization, the filter unit containing the washed product was inserted in a vial containing 2 mL BD Cocktail (Fisher Sci., Model ScintiVerse, Santa Clara, CA) and the amount of $^{14C}$-IPP in each individual filter was quantified by scintillation counting (Beckman Coulter, Model LS 6500, Brea, CA). The average value of the $^{14}$C disintegrations per minute (DPM) count quantifies the cis-prenyl transferase activity of the reaction mixture, as has been well established in native systems (Xie et al, Phytochem. (2008) 69:2539-45; Brasher et al., The Plant J. (2015) 82:903-14; Qu et al, J. Biol. Chem., (2015) 290: 1898-1914; Placido et al, Front. Plant Sci. (2019) doi.org/10.3389/fpls.2019.00760).

Figure 5:
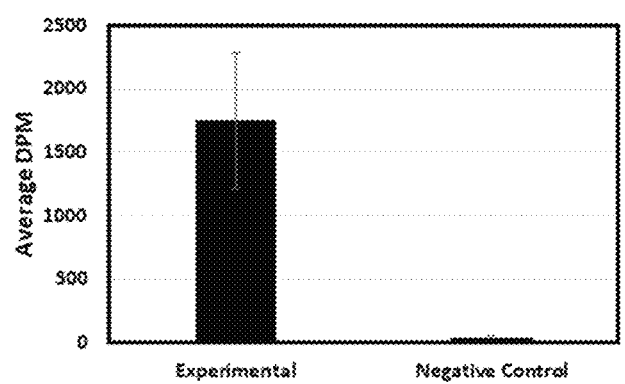
FIG. 5 provides graphical representation of data from in vitro polymerization using *Hevea* recombinant proteins HRT2 (*Hevea* Rubber Transferase 2; homologue to guayule CPT) and HRBP (*Hevea* Rubber Transferase Binding Protein; homologue to guayule CBP). Experimental=recombinant proteins; Negative control=recombinant proteins+40 mM EDTA FIG. 6 provides results from a chromatogram showing elution for THF-soluble reaction components. Polyisoprene molecular weight standards are represented by 1PI1 (1030 g/mole), 3PI3 (12,100 g/mole), 5PI5 (111,000 g/mole) and 7PI7 (1,180,000 g/mole). Reaction product replicates are represented by 2GP1-2, 4GP3-4, and 5GP5-6.

Results are shown in FIG. 5 for experiments utilizing HRT2 (SEQ ID NO: 6) and HRBP (SEQ ID NO: 8) derived from *Hevea*. As stated above, the average value of the $^{14}C$ disintegrations per minute (DPM) count from the polymers produced quantifies the cis-prenyl transferase enzymatic activity. The DPM values for a series of experiments wherein initiator and monomer molecules were introduced into reaction vessels containing various enzymatic and stabilizing components are shown below. The higher the value, the more IPP incorporated into the product under the specific conditions and times.

Characterization of Synthetic Enzyme Complex Reaction Products

Reaction products from this system were evaluated after 23 h incubation. Six reaction vials, each 100 μL, were combined as: 1+2, 3+4, 5+6. 300 uL THF added, gentle shaking at room temperature, 4.5 h. Four synthetic polyisoprene standards were prepared by placing pre-weighed polymer in 3 mL THF each, also shaken. GP1-2, GP3-4, GP5-6 solutions (100 uL, water clear) were pipetted into autosampler vials. Solution was notably viscous. All samples were injected (50 uL load) into the GPC, and chromatograms were collected per standard laboratory procedure.

Figure 6:
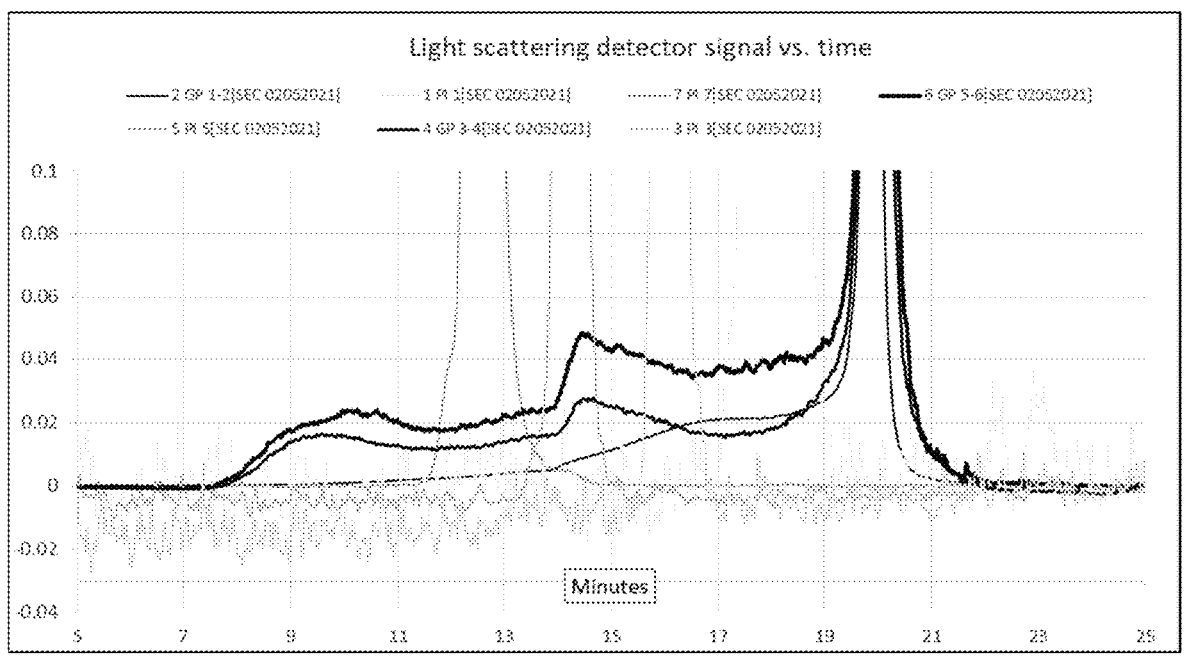
Figure 7:
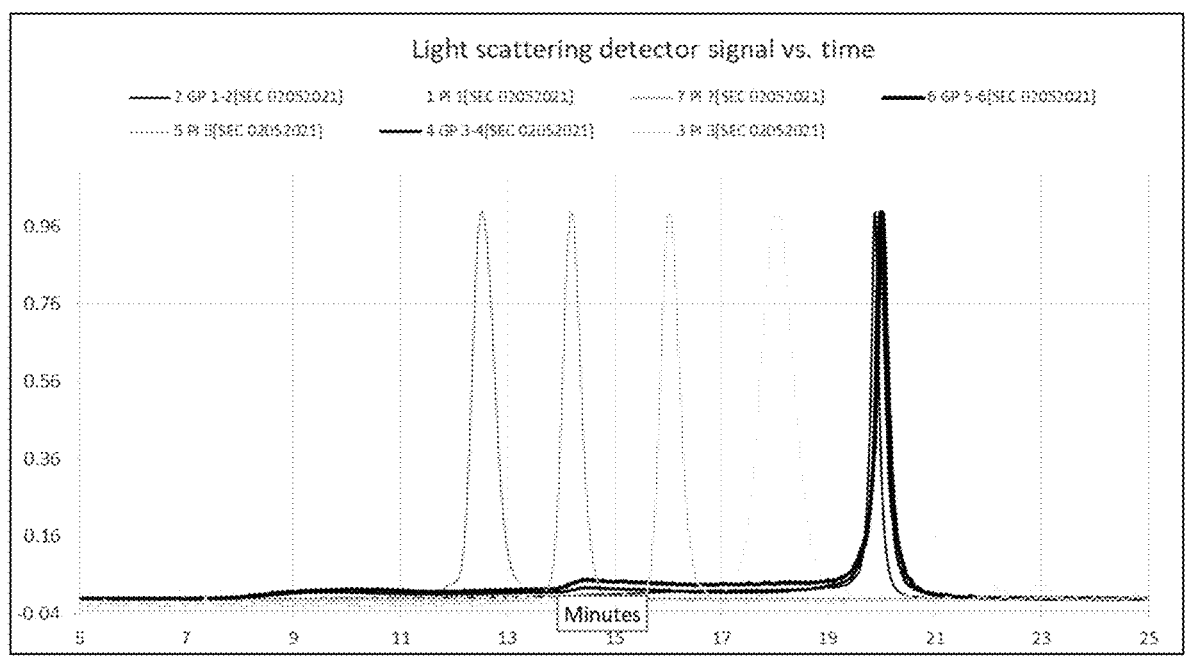
FIG. 7 provides results from a chromatogram showing elution for THF-soluble reaction components, zoomed out, to show the height of the peaks. Polyisoprene molecular weight standards are represented by 1PI1 (1030 g/mole), 3PI3 (12,100 g/mole), 5PI5 (111,000 g/mole) and 7PI7 (1,180,000 g/mole). Reaction product replicates are represented by 2GP1-2, 4GP3-4, and 5GP5-6.

Results are shown in FIG. 6 and FIG. 7. Chromatograms from size-exclusion chromatographic (SEC) separation, which shows the elution of reaction products and synthetic polyisoprene standards. In SEC the larger molecules elute first. The polyisoprene standards serve as a calibration of elution time and molecular weight; elution from ~12 to ~19 minutes corresponded to 1,180,000 to 1030 g/mole. Reaction products from 3 replicate synthetic complex experiments (1+2, 3+4, 5+6) are also shown, and elute from ~8-22 minutes. Similar elution profiles are seen for samples 3+4 and 5+6; sample 1+2 shows a different profile with elution of product beginning ~14 minutes. For all 3 samples, the largest peak occurred at ~20 minutes, interpreted as molecular weights below 1030 g/mole (see inset). Nevertheless, a small but measurable amount of high molecular weight product was detected, in all cases, at ~$10^5$ g/mole. Reaction products (samples 3+4 and 5+6) that elute before 11 minutes represent products larger than $10^6$ g/mole.

While the invention has been described with reference to details of the illustrated embodiments, these details are not intended to limit the scope of the invention as defined in the appended claims.

We claim:

1. A composition for producing rubber polymer in vitro, comprising:
a recombinant cis-prenyltransferase protein with a sequence identity at least 80% identical to SEQ ID NO: 2 obtained from *Parthenium argentatum* or with a sequence identity at least 80% identical to SEQ ID NO: 6 obtained from *Hevea brasiliensis*,
a recombinant cis-prenyltransferase binding protein with a sequence identity at least 80% identical to SEQ ID NO: 4 obtained from *Parthenium argentatum* or a sequence identity at least 80% identical to SEQ ID NO: 8 obtained from *Hevea brasiliensis*,
wherein both said cis-prenyltransferase and cis-prenyltransferase binding proteins are incorporated into a membrane composed of lipid wherein the lipid and proteins form a synthetic molecular complex;
an allylic pyrophosphate reaction initiator;
a monomer-isopentenyl pyrophosphate substrate convertible into a polymer by said cis-prenyltransferase,
and an aqueous medium.

2. The composition of claim 1, wherein the lipid is dimyristoylphosphatidylcholine (DMPC).

3. The composition of claim 1, further comprising a recombinant protein which has a sequence at least 99% identical to SEQ ID NO: 10 or SEQ ID NO: 12.

4. The composition of claim 3, wherein the recombinant protein has a SEQ ID NO: 10 or SEQ ID NO: 12.

5. The composition of claim 1, further comprising a non-aqueous organic solvent.

6. The composition of claim 1, further comprising a divalent cation.

7. The composition of claim 6, wherein the divalent cation is $Mg^{2+}$.

8. The composition of claim 1, wherein the allylic pyrophosphate is farnesyl pyrophosphate FPP.

9. A method of synthesizing rubber polymer, comprising providing reagents for synthesizing the rubber polymer; providing the composition of claim 1; and
contacting the reagents with the composition of claim 1 under conditions allowing for the production of the rubber polymer, thereby synthesizing the rubber polymer.

10. The method of claim 9, wherein the composition of claim 1 further comprises a lipid capable of forming a higher order structure.

11. The method of claim 9, wherein the composition of claim 1 further comprises an isolated and purified small rubber particle protein.

12. The method of claim 9, wherein the composition of claim 1 further comprises an organic solvent.

13. The method of claim 9 further comprising a divalent cation and wherein the divalent cation is optionally $Mg^{2+}$.

14. The composition of claim 1, wherein the allylic pyrophosphate is isopentenyl pyrophosphate.

15. A composition for producing rubber polymer in vitro, comprising:
a recombinant cis-prenyltransferase protein with a sequence at least 95% identical to a SEQ ID NO: 2 or SEQ ID NO: 6 incorporated into a membrane composed of lipid;

a recombinant cis-prenyltransferase binding protein with a sequence at least 95% identical to SEQ ID NO: 4 or SEQ ID NO: 8 incorporated into a membrane composed of lipid; a reaction allylic pyrophosphate initiator; a substrate convertible into a polymer by said cis-prenyltransferase; and an aqueous medium.

16. The composition of claim 15, wherein the lipid is 1,2-Dimyristoyl-sn-glycero-3-phosphocholine (DMPC).

17. The composition of claim 15, further comprising a recombinant protein wherein the protein has a sequence at least 99% identical to SEQ ID NO: 10 or SEQ ID NO: 12.

18. The composition of claim 15, wherein the cis-prenyltransferase has a sequence at least 99% identical to SEQ ID NO: 2 or SEQ ID NO: 6.

19. The composition of claim 15, wherein the cis-prenyltransferase binding protein has a sequence at least 99% identical to SEQ ID NO: 4 or SEQ ID NO: 8.

20. The composition of claim 15, further comprising a non-aqueous organic solvent.

21. The composition of claim 15, further comprising a divalent cation.

22. The composition of claim 21, wherein the divalent cation is magnesium.

23. The composition of claim 22, wherein the allylic pyrophosphate is farnesyl pyrophosphate.

24. The composition of claim 15, further comprising both an aqueous medium and non-aqueous organic solvent.

25. The composition of claim 1, further comprising both an aqueous medium and non-aqueous organic solvent.

* * * * *

SEQUENCE LISTING

```
<160> NUMBER OF SEQ ID NOS: 14

<210> SEQ ID NO 1
<211> LENGTH: 915
<212> TYPE: DNA
<213> ORGANISM: Parthenium argentatum

<400> SEQUENCE: 1
atggaagtca atccaatcat cacaacagat aattccttga aaaaaatgga agaagaaaga      60
tcagaaagta tgatgaccaa gttcttagga ggcttaaatt taacagcaag aaagcttctt     120
tttcgggtca tttcaaccgg cccgattcca caacatatag cattcatcat ggatggaaac     180
cgaagattcg ccaagaaatg gaagctgact gagggtggtg ggcataaagc cggattcttg     240
gcactcatgt cggtgctaaa atactgttat gaaataggtg tgaagtatgt gacggtttac     300
gcattcagtc ttgataactt caataggcgg ccggatgaag ttcagtatgt aatgaacttg     360
atgcaagaaa agattgaagg gtttttgaaa gagttaacaa ttgtgaacaa gtatggtgtt     420
agagtcttgt ttattggtga tcttaaaagg ttatacgagc cggttaggat tgcagccgag     480
aaagcaatgg aagccactgc tcacaacaca catacatatc ttttagtatg tgttgcttac     540
acttcttcac atgagatccc acgtgctatt tacgaagctt gtgaagagaa gagtggtgga     600
acccgagtta tgatgatgaa tgggagtgtg aatggagatt acaataatgg agattatgag     660
gatcatgggg aggggggttaa agtggtggat attgataaac atatgtatat ggcagtggct     720
ccggatcctg atattttggt taggagctcc ggggagacga gactgagcaa ctacttattg     780
tggcaaacca ctaattgtgt gttgtattcg ccaaaagcgt tgtggccgga gatggggctg     840
tggcaggtgg tttgggggat cttgaagttt cagaaggatt ataagtattt ggagaagaag     900
aagaagcagg cttga                                                     915
```

```
<210> SEQ ID NO 2
<211> LENGTH: 304
<212> TYPE: PRT
<213> ORGANISM: Parthenium argentatum

<400> SEQUENCE: 2
```

```
Met Glu Val Asn Pro Ile Ile Thr Thr Asp Asn Ser Leu Lys Lys Met
1               5                   10                  15
Glu Glu Glu Arg Ser Glu Ser Met Met Thr Lys Phe Leu Gly Gly Leu
            20                  25                  30
Asn Leu Thr Ala Arg Lys Leu Leu Phe Arg Val Ile Ser Thr Gly Pro
        35                  40                  45
Ile Pro Gln His Ile Ala Phe Ile Met Asp Gly Asn Arg Arg Phe Ala
    50                  55                  60
Lys Lys Trp Lys Leu Thr Glu Gly Gly His Lys Ala Gly Phe Leu
65                  70                  75                  80
Ala Leu Met Ser Val Leu Lys Tyr Cys Tyr Glu Ile Gly Val Lys Tyr
                85                  90                  95
Val Thr Val Tyr Ala Phe Ser Leu Asp Asn Phe Asn Arg Arg Pro Asp
            100                 105                 110
Glu Val Gln Tyr Val Met Asn Leu Met Gln Glu Lys Ile Glu Gly Phe
        115                 120                 125
Leu Lys Glu Leu Thr Ile Val Asn Lys Tyr Gly Val Arg Val Leu Phe
    130                 135                 140
Ile Gly Asp Leu Lys Arg Leu Tyr Glu Pro Val Arg Ile Ala Ala Glu
145                 150                 155                 160
Lys Ala Met Glu Ala Thr Ala His Asn Thr His Thr Tyr Leu Leu Val
                165                 170                 175
Cys Val Ala Tyr Thr Ser Ser His Glu Ile Pro Arg Ala Ile Tyr Glu
            180                 185                 190
Ala Cys Glu Glu Lys Ser Gly Gly Thr Arg Val Met Met Met Asn Gly
        195                 200                 205
Ser Val Asn Gly Asp Tyr Asn Asn Gly Asp Tyr Glu Asp His Gly Glu
    210                 215                 220
Gly Val Lys Val Val Asp Ile Asp Lys His Met Tyr Met Ala Val Ala
225                 230                 235                 240
Pro Asp Pro Asp Ile Leu Val Arg Ser Ser Gly Glu Thr Arg Leu Ser
                245                 250                 255
Asn Tyr Leu Leu Trp Gln Thr Thr Asn Cys Val Leu Tyr Ser Pro Lys
            260                 265                 270
Ala Leu Trp Pro Glu Met Gly Leu Trp Gln Val Val Trp Gly Ile Leu
        275                 280                 285
Lys Phe Gln Lys Asp Tyr Lys Tyr Leu Glu Lys Lys Lys Gln Ala
    290                 295                 300
```

<210> SEQ ID NO 3
<211> LENGTH: 753
<212> TYPE: DNA
<213> ORGANISM: Parthenium argentatum

<400> SEQUENCE: 3

```
atggatctag tagctgaatc acagaagttt tttcgcagga cctcgcagag tggcagcatt      60
gtgctcttct tgctctggca tgtagttcac ttaacaatca gtgttttata cattgtccgg     120
gagatctttc gtgcgattga aagctacctt ataacaaacg gatatgtgaa acatacaca     180
aatataaatt tacaacgggt caaatatctt ggaattgttg tggacagtga tgaagcccgt     240
aacatctcaa aagtggttga actttagag tggctttcag ctataggtgt gaaaaagatc     300
tgtctttatg accgggaagg agtgttgaag aagtcaaagg cggtcatcat ggagagattt     360
ggctctacag agacttccaa tgatagtgca gtagccaatc cactaagtaa aaaacggatg     420
```

```
gattttgaat tgtttcaat cactgatggc aaagaagcag ttgctaaagc agctaaccta    480
ctctttaaaa aatattatgt ggacgaagat tcagaaaaac cattctttac tgaaacccac    540
ttgaccgagg cactaaagac cctcgggcaa gtagagccag atcccgatct tttattaatt    600
tacgggccag tgaggtgcca ccttggtttt ccagcatggc gacttcgtta cacggagatg    660
gtgcacatgg gaccattaaa gtacaagaaa tttggtttga ttctgaaagc aattcacagg    720
ttcactaagg tgaagcaaaa ctatggttca taa                                  753
```

```
<210> SEQ ID NO 4
<211> LENGTH: 250
<212> TYPE: PRT
<213> ORGANISM: Parthenium argentatum

<400> SEQUENCE: 4

Met Asp Leu Val Ala Glu Ser Gln Lys Phe Phe Arg Arg Thr Ser Gln
1               5                   10                  15

Ser Gly Ser Ile Val Leu Phe Leu Leu Trp His Val Val His Leu Thr
            20                  25                  30

Ile Ser Val Leu Tyr Ile Val Arg Glu Ile Phe Arg Ala Ile Glu Ser
        35                  40                  45

Tyr Leu Ile Thr Asn Gly Tyr Val Lys Thr Tyr Thr Asn Ile Asn Leu
    50                  55                  60

Gln Arg Val Lys Tyr Leu Gly Ile Val Val Asp Ser Asp Glu Ala Arg
65                  70                  75                  80

Asn Ile Ser Lys Val Val Glu Leu Leu Glu Trp Leu Ser Ala Ile Gly
                85                  90                  95

Val Lys Lys Ile Cys Leu Tyr Asp Arg Glu Gly Val Leu Lys Lys Ser
            100                 105                 110

Lys Ala Val Ile Met Glu Arg Phe Gly Ser Thr Glu Thr Ser Asn Asp
        115                 120                 125

Ser Ala Val Ala Asn Pro Leu Ser Lys Lys Arg Met Asp Phe Glu Phe
    130                 135                 140

Val Ser Ile Thr Asp Gly Lys Glu Ala Val Ala Lys Ala Ala Asn Leu
145                 150                 155                 160

Leu Phe Lys Lys Tyr Tyr Val Asp Glu Asp Ser Glu Lys Pro Phe Phe
                165                 170                 175

Thr Glu Thr His Leu Thr Glu Ala Leu Lys Thr Leu Gly Gln Val Glu
            180                 185                 190

Pro Asp Pro Asp Leu Leu Leu Ile Tyr Gly Pro Val Arg Cys His Leu
        195                 200                 205

Gly Phe Pro Ala Trp Arg Leu Arg Tyr Thr Glu Met Val His Met Gly
    210                 215                 220

Pro Leu Lys Tyr Lys Lys Phe Gly Leu Ile Leu Lys Ala Ile His Arg
225                 230                 235                 240

Phe Thr Lys Val Lys Gln Asn Tyr Gly Ser
                245                 250

<210> SEQ ID NO 5
<211> LENGTH: 1051
<212> TYPE: DNA
<213> ORGANISM: Hevea brasiliensis

<400> SEQUENCE: 5
tggaggattt accgagtcac ctacaggctt cgggttaagt cagtggttta aggaaaatgg     60
aattatacaa cggtgagagg ccaagtgtgt tcagactttt agggaagtat atgagaaaag    120
```

```
ggttatatag catcctaacc cagggtccca tccctactca tattgccttc atattggatg      180
gaaacgggag gtttgctaag aagcataaac tgccagaagg aggtggtcat aaggctggat      240
ttttagctct tctgaacgta ctaacttatt gctatgagtt aggagtgaaa tatgcgacta      300
tctatgcctt tagcatcgat aattttcgaa ggaaacctca tgaggttcag tacgtaatga      360
atctaatgct ggagaagatt gaagggatga tcatggaaga agtatcatc aatgcatatg       420 atatttgcgt gcgttttgtt ggtaatctga agcttttaga tgagccactc aagaccgcag      480
cagataagat aatgagggct actgccaaaa attccaaatt tgtgcttctc cttgctgtat      540
gctacacttc aactgatgag atcgtgcatg ctgttgaaga atcctctaag gataaattga      600
aatccgatga aatttgcaac gatggaaacg gagattgtgt gattaaaatt gaggagatgg      660
agccatattc tgaaataaaa cttgtagagc ttgagagaaa cacttacata aatccttatc      720
ctgatgtctt gattcgaact tctggggaga cccgtctgag caactaccta ctttggcaga      780
ctactaattg catactgtat tctcctcatg cactgtggcc agagattggt cttcgacacg      840
tggtgtgggc agtaattaac tgccaacgtc attattctta cttggagaaa cataaggaat      900
acttaaaata atttgtttct gttcctagct catcctgcct tattcgcgat agttaagctt      960
aagcatatcc ttgtagaata aacttggaaa ctcaagcaag ggattaatcc ttgtattgta     1020
gcaaattccg acatgcaaaa aaaaaaaaaa a                                    1051

<210> SEQ ID NO 6
<211> LENGTH: 284
<212> TYPE: PRT
<213> ORGANISM: Hevea brasiliensis

<400> SEQUENCE: 6

Met Glu Leu Tyr Asn Gly Glu Arg Pro Ser Val Phe Arg Leu Leu Gly
1               5                   10                  15

Lys Tyr Met Arg Lys Gly Leu Tyr Ser Ile Leu Thr Gln Gly Pro Ile
            20                  25                  30

Pro Thr His Ile Ala Phe Ile Leu Asp Gly Asn Gly Arg Phe Ala Lys
        35                  40                  45

Lys His Lys Leu Pro Glu Gly Gly His Lys Ala Gly Phe Leu Ala
    50                  55                  60

Leu Leu Asn Val Leu Thr Tyr Cys Tyr Glu Leu Gly Val Lys Tyr Ala
65                  70                  75                  80

Thr Ile Tyr Ala Phe Ser Ile Asp Asn Phe Arg Arg Lys Pro His Glu
                85                  90                  95

Val Gln Tyr Val Met Asn Leu Met Leu Glu Lys Ile Glu Gly Met Ile
            100                 105                 110

Met Glu Glu Ser Ile Ile Asn Ala Tyr Asp Ile Cys Val Arg Phe Val
        115                 120                 125

Gly Asn Leu Lys Leu Leu Asp Glu Pro Leu Lys Thr Ala Ala Asp Lys
    130                 135                 140

Ile Met Arg Ala Thr Ala Lys Asn Ser Lys Phe Val Leu Leu Leu Ala
145                 150                 155                 160

Val Cys Tyr Thr Ser Thr Asp Glu Ile Val His Ala Val Glu Glu Ser
                165                 170                 175

Ser Lys Asp Lys Leu Lys Ser Asp Glu Ile Cys Asn Asp Gly Asn Gly
            180                 185                 190

Asp Cys Val Ile Lys Ile Glu Glu Met Glu Pro Tyr Ser Glu Ile Lys
        195                 200                 205
```

Leu Val Glu Leu Glu Arg Asn Thr Tyr Ile Asn Pro Tyr Pro Asp Val
          210                 215                 220

Leu Ile Arg Thr Ser Gly Glu Thr Arg Leu Ser Asn Tyr Leu Leu Trp
225                 230                 235                 240

Gln Thr Thr Asn Cys Ile Leu Tyr Ser Pro His Ala Leu Trp Pro Glu
                245                 250                 255

Ile Gly Leu Arg His Val Val Trp Ala Val Ile Asn Cys Gln Arg His
                260                 265                 270

Tyr Ser Tyr Leu Glu Lys His Lys Glu Tyr Leu Lys
            275                 280

<210> SEQ ID NO 7
<211> LENGTH: 774
<212> TYPE: DNA
<213> ORGANISM: Hevea brasiliensis

<400> SEQUENCE: 7
atggatttga aacctggagc tggagggcag agagttaatc gtttagtgga tccgattagt      60
tatcattttc ttcaatttct gtggcgtact ctacatcttc ttgtcagctt atggtacctt     120
caagttagta tggtccaaat gatcgaaggc tttctaatct tagtggact tgtgaaacgc      180 tatggagccc tcgatattga caaggtccgg taccttgcca ttgtggtaga tagtgaagaa     240
gcttaccaaa tttctaaagt tattcagctt ttgaaatggg tggaagatat gggtgtgaaa     300
catttatgcc tctatgattc aaaaggagtt ctcaagacaa caagaaaac catcatggag       360 agtttgaaca tgctatgcc atttgaggaa gcagttgaaa aagatgtttt actggaccag      420
aaacagatga ctgtggaatt tgcttccagc tccgatggaa aggaagcaat aaccagggca     480
gctaacgtac tctttatgaa gtatttgaag atgctaaaa ctggtgtagg aaaggaagaa       540
ccatgcttta cagaagatca aatggatgag gcactaaaag ctataggtta caagggccg       600 gaacctgact tgctattaat ttatggacct gttagatgcc atctaggttt ctcaccgtgg     660
agacttcgat atactgagat ggtgcatatg ggaccctga ggtacatgaa cctcggttca       720
ctaaaaaagg ccattcacag gttcacaaca gtgcagcaaa attatggtac atga           774

<210> SEQ ID NO 8
<211> LENGTH: 257
<212> TYPE: PRT
<213> ORGANISM: Hevea brasiliensis

<400> SEQUENCE: 8

Met Asp Leu Lys Pro Gly Ala Gly Gly Gln Arg Val Asn Arg Leu Val
1               5                   10                  15

Asp Pro Ile Ser Tyr His Phe Leu Gln Phe Leu Trp Arg Thr Leu His
            20                  25                  30

Leu Leu Val Ser Leu Trp Tyr Leu Gln Val Ser Met Val Gln Met Ile
        35                  40                  45

Glu Gly Phe Leu Ile Ser Ser Gly Leu Val Lys Arg Tyr Gly Ala Leu
    50                  55                  60

Asp Ile Asp Lys Val Arg Tyr Leu Ala Ile Val Val Asp Ser Glu Glu
65                  70                  75                  80

Ala Tyr Gln Ile Ser Lys Val Ile Gln Leu Leu Lys Trp Val Glu Asp
                85                  90                  95

Met Gly Val Lys His Leu Cys Leu Tyr Asp Ser Lys Gly Val Leu Lys
            100                 105                 110

| | | | | | | | | | | | |
|---|---|---|---|---|---|---|---|---|---|---|---|
|Thr|Asn|Lys|Lys|Thr|Ile|Met|Glu|Ser|Leu|Asn|Asn|Ala|Met|Pro|Phe|
| | |115| | | |120| | | |125| |
|Glu|Glu|Ala|Val|Glu|Lys|Asp|Val|Leu|Leu|Asp|Gln|Lys|Gln|Met|Thr|
| |130| | | | |135| | | | |140| |
|Val|Glu|Phe|Ala|Ser|Ser|Asp|Gly|Lys|Glu|Ala|Ile|Thr|Arg|Ala|
|145| | | | |150| | | | |155| | | |160|
|Ala|Asn|Val|Leu|Phe|Met|Lys|Tyr|Leu|Lys|Tyr|Ala|Lys|Thr|Gly|Val|
| | | | |165| | | | |170| | | | |175| |
|Gly|Lys|Glu|Glu|Pro|Cys|Phe|Thr|Glu|Asp|Gln|Met|Asp|Glu|Ala|Leu|
| | | |180| | | | |185| | | | |190| |
|Lys|Ala|Ile|Gly|Tyr|Lys|Gly|Pro|Glu|Pro|Asp|Leu|Leu|Leu|Ile|Tyr|
| | |195| | | | |200| | | | |205| |
|Gly|Pro|Val|Arg|Cys|His|Leu|Gly|Phe|Ser|Pro|Trp|Arg|Leu|Arg|Tyr|
| |210| | | | |215| | | | |220| |
|Thr|Glu|Met|Val|His|Met|Gly|Pro|Leu|Arg|Tyr|Met|Asn|Leu|Gly|Ser|
|225| | | | |230| | | | |235| | | | |240|
|Leu|Lys|Lys|Ala|Ile|His|Arg|Phe|Thr|Thr|Val|Gln|Gln|Asn|Tyr|Gly|
| | | | |245| | | | |250| | | | |255| |
|Thr|

```
<210> SEQ ID NO 9
<211> LENGTH: 912
<212> TYPE: DNA
<213> ORGANISM: Parthenium argentatum

<400> SEQUENCE: 9
ttcttctcct attccttatt gtaatctccg tcactacaaa cttctgttct tctagacgct      60
catggccgaa cctgaatcca atcagtccgc ccagcccgtg gcagagaggg atggggaga     120
ggagcaactg catctgaaat atcttgattt tgtgcaaaac gctgtgatct attttgttgt     180
ttgtttctct actgtttacg gttacgcaaa ggagaacgcc ggttcgtgga agcctggtgt     240
tcaaaccgtt gagaacaccg ttctaaacgt cgttggaccg gtttacgaaa agtattatga     300
ctatcctata gaggccctca agttccttga tgtaaaggtg ggcgacttgg tgaccgagct     360
gaaacggcac gtgccatcac taatgaaaca ggcttcaagc caagccaaat acacggctca     420
gaaccttcca gaagtggcta aagccttggc aacagaggca ttcaaaactg ctacaaatgt     480
ggccaacaca ttgtacgtaa atgcgagcc aacagctaaa cagctataca tgaactacga     540
gccggtagct gagaaataca cggtgtcgac atggcggtca ttgaacaaac tccctttgtt     600
tcctcaggta gctcagattg cggttcctac tggtgcttat gtgcttgaga agtataacga     660
ccccgttagc tacactgcgg acaaaggtta tgctgtggct cagtatttac cgttggttcc     720
gattgataaa attgctaagg tgtttaaaaa gggtgagagc gggtcaacgg ttggtcaaag     780
tggttaggtc gagacttgat gaattacgtt ggttccagtt tataaatcaa gtctatgata     840
atggtttagt tttaaaaaaa aaaaaaaaa aaaaaaaaaa aaaaaaaaa aaaaaaaaa        900
aaaaaaaaaa aa                                                          912

<210> SEQ ID NO 10
<211> LENGTH: 241
<212> TYPE: PRT
<213> ORGANISM: Parthenium argentatum

<400> SEQUENCE: 10
```

| | | | | | | | | | | | | |
|---|---|---|---|---|---|---|---|---|---|---|---|---|
|Met|Ala|Glu|Pro|Glu|Ser|Asn|Gln|Ser|Ala|Gln|Pro|Val|Ala|Glu|Arg|
|1| | | |5| | | | |10| | | | |15| |

Asp Gly Gly Glu Glu Gln Leu His Leu Lys Tyr Leu Asp Phe Val Gln
            20                  25                  30

Asn Ala Val Ile Tyr Phe Val Cys Phe Ser Thr Val Tyr Gly Tyr
        35                  40                  45

Ala Lys Glu Asn Ala Gly Ser Trp Lys Pro Val Gln Thr Val Glu
 50                  55                  60

Asn Thr Val Leu Asn Val Val Gly Pro Val Tyr Glu Lys Tyr Asp
 65                  70                  75                  80

Tyr Pro Ile Glu Ala Leu Lys Phe Leu Asp Val Lys Val Gly Asp Leu
                85                  90                  95

Val Thr Glu Leu Lys Arg His Val Pro Ser Leu Met Lys Gln Ala Ser
            100                 105                 110

Ser Gln Ala Lys Tyr Thr Ala Gln Asn Leu Pro Glu Val Ala Lys Ala
            115                 120                 125

Leu Ala Thr Glu Ala Phe Lys Thr Ala Thr Asn Val Ala Asn Thr Leu
130                 135                 140

Tyr Val Lys Cys Glu Pro Thr Ala Lys Gln Leu Tyr Met Asn Tyr Glu
145                 150                 155                 160

Pro Val Ala Glu Lys Tyr Thr Val Ser Thr Trp Arg Ser Leu Asn Lys
                165                 170                 175

Leu Pro Leu Phe Pro Gln Val Ala Gln Ile Ala Val Pro Thr Gly Ala
            180                 185                 190

Tyr Val Leu Glu Lys Tyr Asn Asp Pro Val Ser Tyr Thr Ala Asp Lys
            195                 200                 205

Gly Tyr Ala Val Ala Gln Tyr Leu Pro Leu Val Pro Ile Asp Lys Ile
210                 215                 220

Ala Lys Val Phe Lys Lys Gly Glu Ser Gly Ser Thr Val Gly Gln Ser
225                 230                 235                 240

Gly

<210> SEQ ID NO 11
<211> LENGTH: 910
<212> TYPE: DNA
<213> ORGANISM: Hevea brasiliensis

<400> SEQUENCE: 11
cagtgttttc cgaaaggcaa atctttttc aaacttcagc gactgcgttt tgaatttgtg      60
atttttaaag gaatttttca attatggctg aagaggtgga ggaagagagg ctaaagtatt     120
tggattttgt gcgagcggct ggagtttatg ctgtagattc tttctcaact ctctaccttt     180
atgccaagga catatctggt ccattaaaac ctggtgtcga tactattgag aatgtggtga     240
agaccgtggt tactcctgtt tattatattc cccttgaggc tgtcaagttt gtagacaaaa     300
cggtggatgt atcggtcact agcctagatg gcgttgttcc cccagttatc aagcaggtgt     360
ctgcccaaac ttactcggta gctcaagatg ctccaagaat tgttcttgat gtggcttctt     420
cagttttcaa cactggtgtg caggaaggcg caaaagctct gtacgctaat cttgaaccaa     480
aagctgagca atatgcggtc attacctggc gtgccctcaa taagctgcca ctagttcctc     540
aagtggcaaa tgtagttgtg ccaaccgctg tttattctc tgaaaagtac aacgatgttg     600
ttcgtggcac tactgagcag ggatatagag tgtcctctta tttgcctttg ttgcccactg     660
agaaaattac taaggtgttt ggagatgagg catcataatc tgcactggat tggttatttt     720
atctattgtg agctttttta tatgtactta ttcagtgttt agaataagtc tttggtggtg     780

```
tgttttggat gtggaataaa gggccaattg cattgttggt caatatataa ttatgtataa    840
catttcgtga tttgagttgg aatctaaagg ttttattaag aatggatgga ctaaaaaaaa    900
aaaaaaaaaa                                                           910
```

<210> SEQ ID NO 12
<211> LENGTH: 204
<212> TYPE: PRT
<213> ORGANISM: Hevea brasiliensis

<400> SEQUENCE: 12

```
Met Ala Glu Glu Val Glu Glu Arg Leu Lys Tyr Leu Asp Phe Val
1               5                   10                  15

Arg Ala Ala Gly Val Tyr Ala Val Asp Ser Phe Ser Thr Leu Tyr Leu
                20                  25                  30

Tyr Ala Lys Asp Ile Ser Gly Pro Leu Lys Pro Gly Val Asp Thr Ile
            35                  40                  45

Glu Asn Val Val Lys Thr Val Val Thr Pro Val Tyr Tyr Ile Pro Leu
 50                  55                  60

Glu Ala Val Lys Phe Val Asp Lys Thr Val Asp Val Ser Val Thr Ser
65                  70                  75                  80

Leu Asp Gly Val Val Pro Pro Val Ile Lys Gln Val Ser Ala Gln Thr
                85                  90                  95

Tyr Ser Val Ala Gln Asp Ala Pro Arg Ile Val Leu Asp Val Ala Ser
            100                 105                 110

Ser Val Phe Asn Thr Gly Val Gln Glu Gly Ala Lys Ala Leu Tyr Ala
        115                 120                 125

Asn Leu Glu Pro Lys Ala Glu Gln Tyr Ala Val Ile Thr Trp Arg Ala
130                 135                 140

Leu Asn Lys Leu Pro Leu Val Pro Gln Val Ala Asn Val Val Val Pro
145                 150                 155                 160

Thr Ala Val Tyr Phe Ser Glu Lys Tyr Asn Asp Val Val Arg Gly Thr
                165                 170                 175

Thr Glu Gln Gly Tyr Arg Val Ser Ser Tyr Leu Pro Leu Leu Pro Thr
            180                 185                 190

Glu Lys Ile Thr Lys Val Phe Gly Asp Glu Ala Ser
        195                 200
```

<210> SEQ ID NO 13
<211> LENGTH: 681
<212> TYPE: DNA
<213> ORGANISM: Hevea brasiliensis

<400> SEQUENCE: 13

```
ttttgatctt ccattttgc aaaaggaaat cttcgattat ggctgaagac gaagacaacc     60
aacaagggca gggggagggg ttaaaatatt tgggttttgt gcaagacgcg gcaacttatg    120
ctgtgactac cttctcaaac gtctatcttt ttgccaaaga caaatctggt ccactgcagc    180
ctggtgtcga tatcattgag ggtccggtga agaacgtggc tgtacctctc tataataggt    240
tcagttatat tcccaatgga gctctcaagt ttgtagacag cacggttgtt gcatctgtca    300
ctattataga tcgctctctt cccccaattg tcaaggacgc atctatccaa gttgtttcag    360
caattcgagc tgccccagaa gctgctcgtt ctctggcttc ttctttgcct gggcagacca    420
agatacttgc taaggtgttt tatggagaga attgagcccc aatttgcacc aattgcttcc    480
aactaagcaa gttaatgata tgctcaagaa tatatatcta ttgtgagctt tttttatgtt    540
```

-continued

```
ctcatcctga gtgttgagac tatgttttcg tttgaatatt atactgtgtt ttattatgtg       600
ttttgaatat tcataatgag aataaagggc caattgaatt attggccaat atgtaatgat       660
acataaattt cgtgattgag t                                                  681

<210> SEQ ID NO 14
<211> LENGTH: 138
<212> TYPE: PRT
<213> ORGANISM: Hevea brasiliensis

<400> SEQUENCE: 14

Met Ala Glu Asp Glu Asp Asn Gln Gln Gly Gln Gly Glu Gly Leu Lys
1               5                   10                  15

Tyr Leu Gly Phe Val Gln Asp Ala Ala Thr Tyr Ala Val Thr Thr Phe
            20                  25                  30

Ser Asn Val Tyr Leu Phe Ala Lys Asp Lys Ser Gly Pro Leu Gln Pro
        35                  40                  45

Gly Val Asp Ile Ile Glu Gly Pro Val Lys Asn Val Ala Val Pro Leu
    50                  55                  60

Tyr Asn Arg Phe Ser Tyr Ile Pro Asn Gly Ala Leu Lys Phe Val Asp
65                  70                  75                  80

Ser Thr Val Val Ala Ser Val Thr Ile Ile Asp Arg Ser Leu Pro Pro
                85                  90                  95

Ile Val Lys Asp Ala Ser Ile Gln Val Val Ser Ala Ile Arg Ala Ala
            100                 105                 110

Pro Glu Ala Ala Arg Ser Leu Ala Ser Ser Leu Pro Gly Gln Thr Lys
        115                 120                 125

Ile Leu Ala Lys Val Phe Tyr Gly Glu Asn
    130                 135
```